(12) United States Patent
Cepress

(10) Patent No.: US 11,786,250 B2
(45) Date of Patent: Oct. 17, 2023

(54) COLLAR FOR SECURING CIRCULAR SURGICAL STAPLER END EFFECTOR TO SHAFT

(71) Applicant: Cilag GmbH International, Zug (CH)

(72) Inventor: Jonathan M. Cepress, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/496,202

(22) Filed: Oct. 7, 2021

(65) Prior Publication Data
US 2023/0112467 A1 Apr. 13, 2023

(51) Int. Cl.
*A61B 17/115* (2006.01)
*A61B 17/3205* (2006.01)
*A61B 17/00* (2006.01)

(52) U.S. Cl.
CPC .... *A61B 17/1155* (2013.01); *A61B 17/32053* (2013.01); *A61B 2017/0046* (2013.01); *A61B 2017/00477* (2013.01)

(58) Field of Classification Search
CPC .. A61B 17/1155; A61B 17/115; A61B 17/068
See application file for complete search history.

(56) References Cited

U.S. PATENT DOCUMENTS

| | | | | |
|---|---|---|---|---|
| 3,552,626 A | * | 1/1971 | Astafiev | A61B 17/1155 227/19 |
| 4,289,133 A | * | 9/1981 | Rothfuss | A61B 17/115 227/175.3 |
| 4,304,236 A | * | 12/1981 | Conta | A61B 17/115 227/19 |
| 4,476,863 A | * | 10/1984 | Kanshin | A61B 17/115 606/171 |
| 4,603,693 A | * | 8/1986 | Conta | A61B 17/1155 227/179.1 |
| 5,292,053 A | | 3/1994 | Bilotti et al. | |
| 5,333,773 A | | 8/1994 | Main et al. | |
| 5,350,104 A | | 9/1994 | Main et al. | |
| 5,533,661 A | | 7/1996 | Main et al. | |

(Continued)

FOREIGN PATENT DOCUMENTS

EP 2967568 B1 11/2018

OTHER PUBLICATIONS

International Search Report and Written Opinion dated Dec. 16, 2022, for International Application No. PCT/IB2022/059453, 15 pages.

*Primary Examiner* — Gloria R Weeks
(74) *Attorney, Agent, or Firm* — Frost Brown Todd LLP

(57) ABSTRACT

A surgical instrument includes a shaft assembly, a stapling assembly disposed at a distal end of the shaft assembly and extending along a central axis, and an anvil configured to selectively couple with the stapling assembly to compress a tissue and form staples in the tissue. The stapling assembly includes a housing assembly that includes a proximal housing and a distal housing. The proximal housing is secured to the shaft assembly and is separable from the distal housing to thereby releasably couple the distal housing with the shaft assembly. The stapling assembly further includes a deck member having an annular array of staple openings configured to receive a plurality of staples, and a knife member at least partially disposed within the housing assembly.

20 Claims, 16 Drawing Sheets

(56) References Cited

U.S. PATENT DOCUMENTS

| | | |
|---|---|---|
| 8,910,847 B2 | 12/2014 | Nalagatla et al. |
| 9,713,469 B2 | 7/2017 | Leimbach et al. |
| 9,907,552 B2 | 3/2018 | Measamer et al. |
| 9,913,643 B2 * | 3/2018 | Penna ................. A61B 17/1155 |
| 9,936,949 B2 | 4/2018 | Measamer et al. |
| 10,542,990 B2 * | 1/2020 | Swayze .............. A61B 17/1155 |
| 10,709,452 B2 | 7/2020 | DiNardo et al. |
| 2015/0083772 A1 | 3/2015 | Miller et al. |
| 2017/0105736 A1 * | 4/2017 | Chen ................. A61B 17/1155 |
| 2018/0132849 A1 | 5/2018 | Miller et al. |

* cited by examiner

COLLAR FOR SECURING CIRCULAR SURGICAL STAPLER END EFFECTOR TO SHAFT

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018, now abandoned; and U.S. Pat. No. 10,709,452, entitled "Methods and Systems for Performing Circular Stapling," issued Jul. 14, 2020. The disclosure of each of the above-cited U.S. patent Publications and U.S. patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
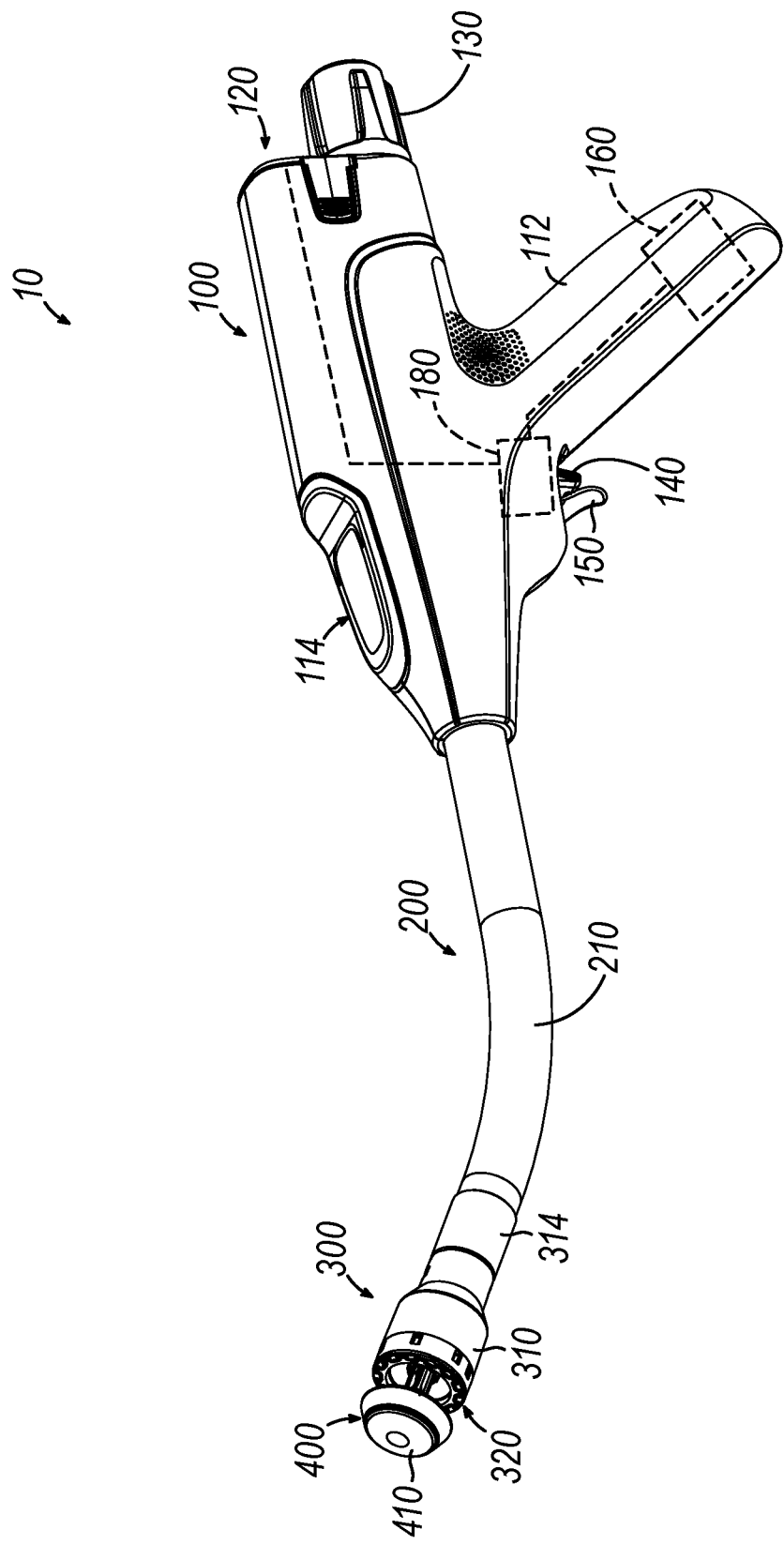
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
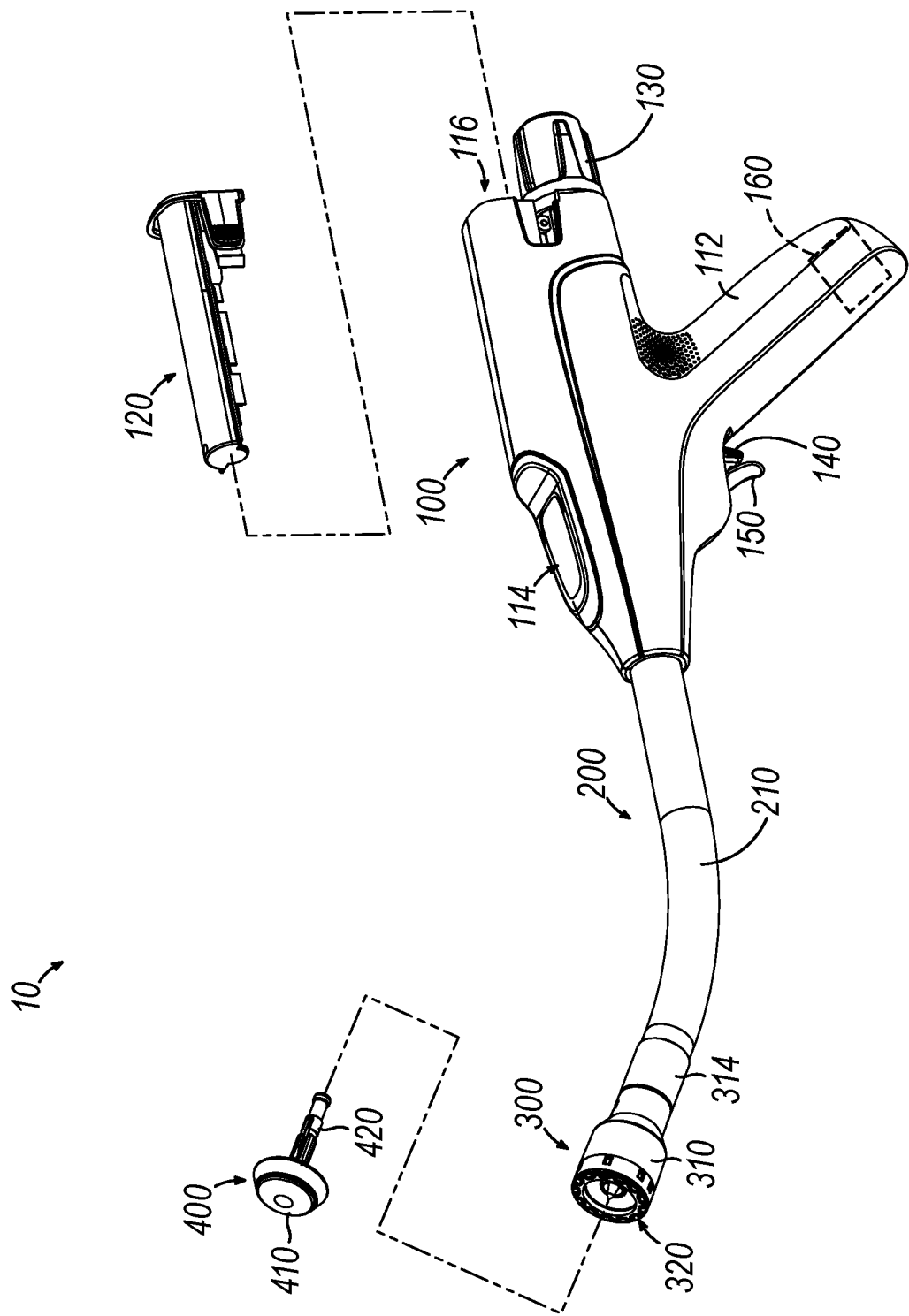
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
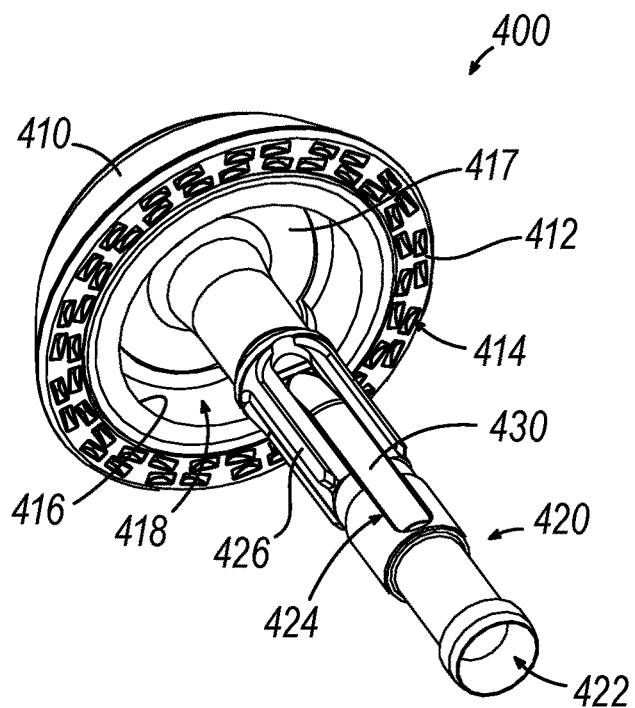
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 4:
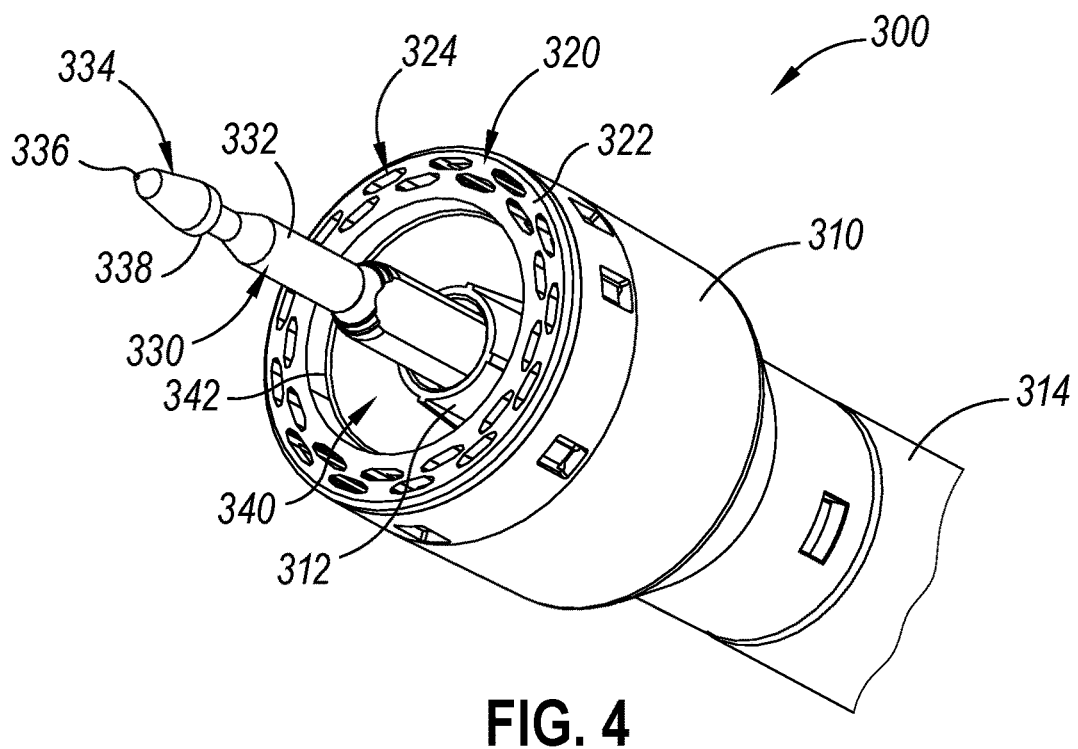
FIG. 4 depicts a perspective view of the stapling head assembly of the circular stapler of FIG. 1.
Figure 5:
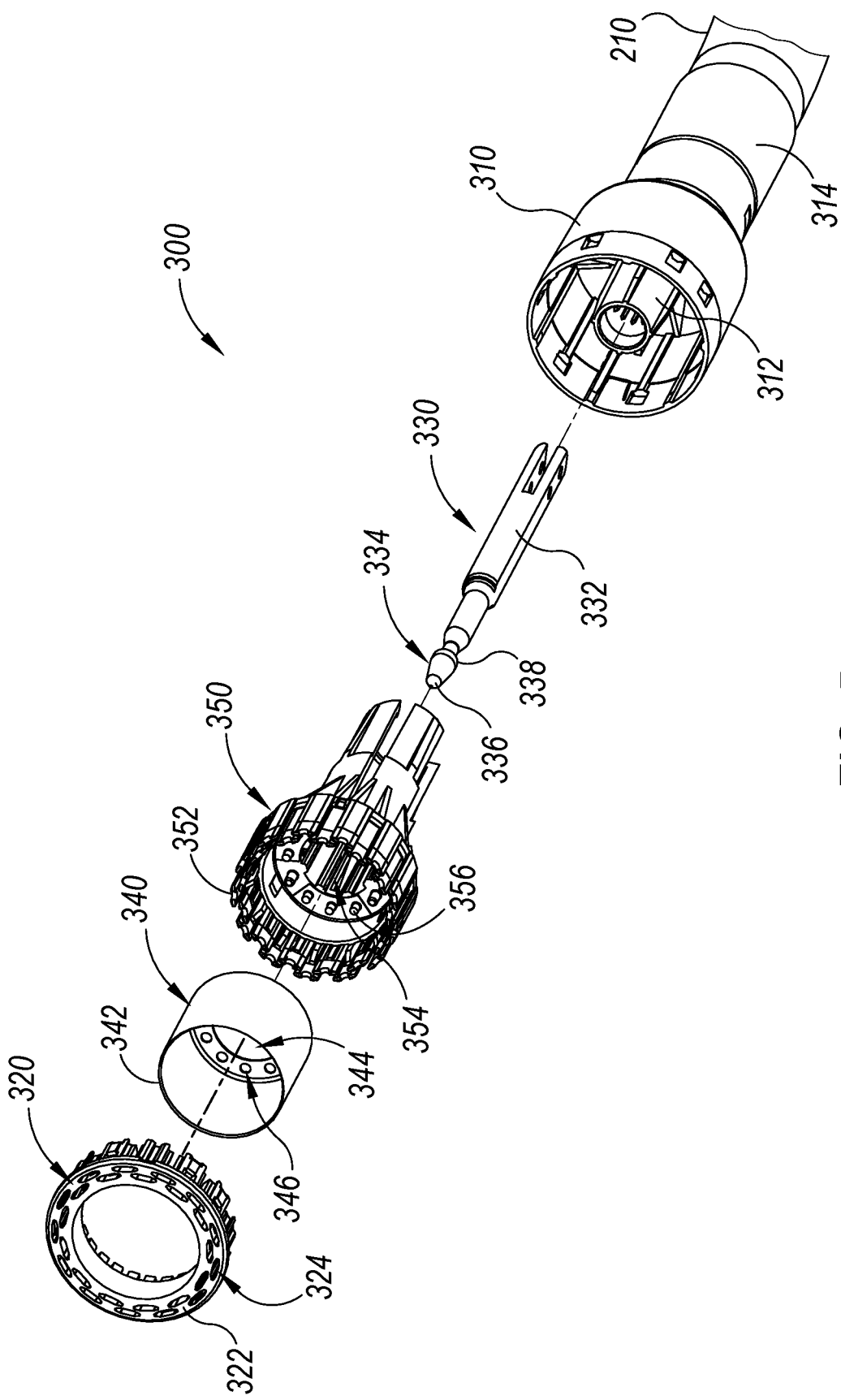
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200) via a sleeve (314), and thus body member (310), sleeve (314), and outer sheath (210) cooperate to establish a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 4, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
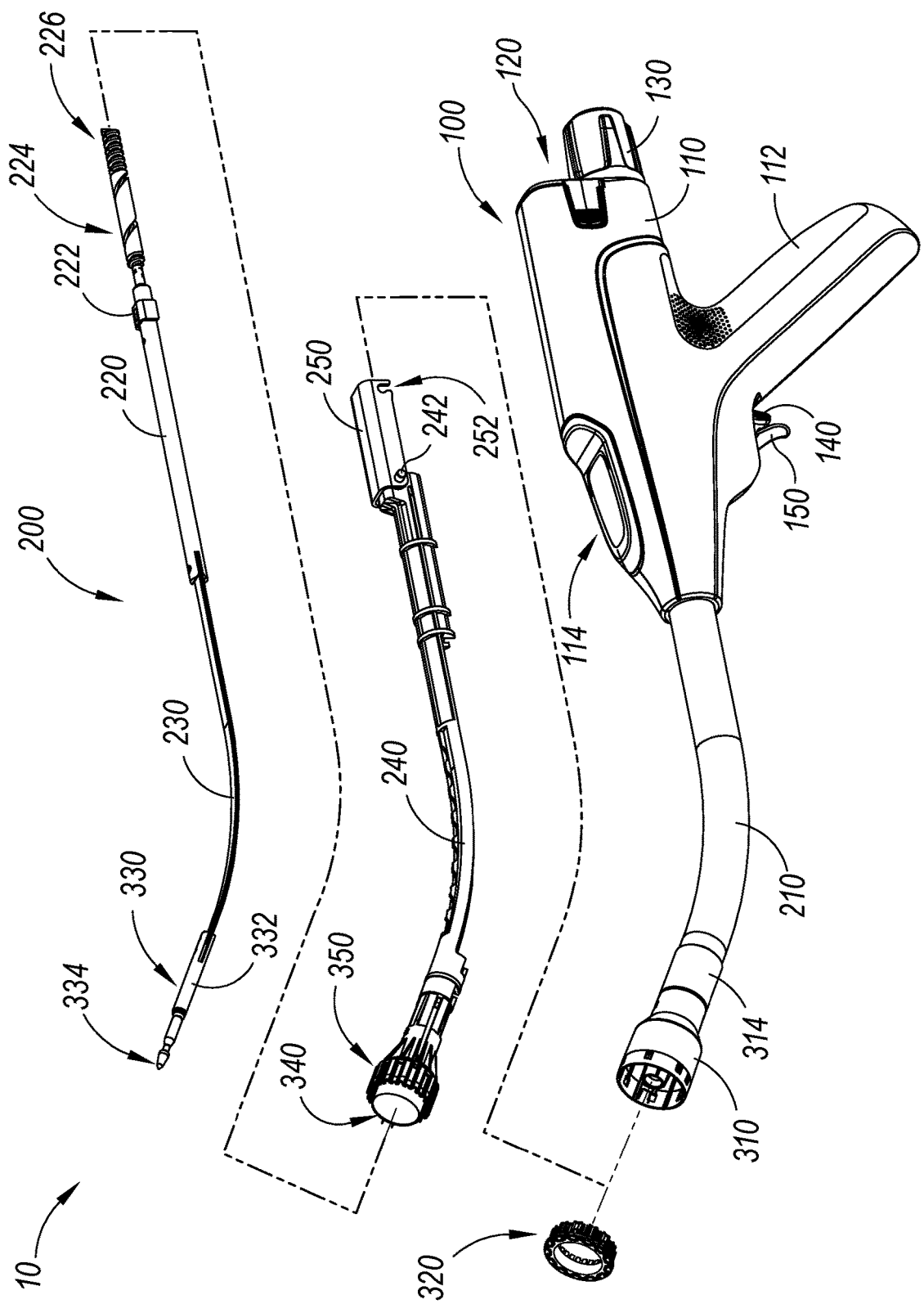
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150)

is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
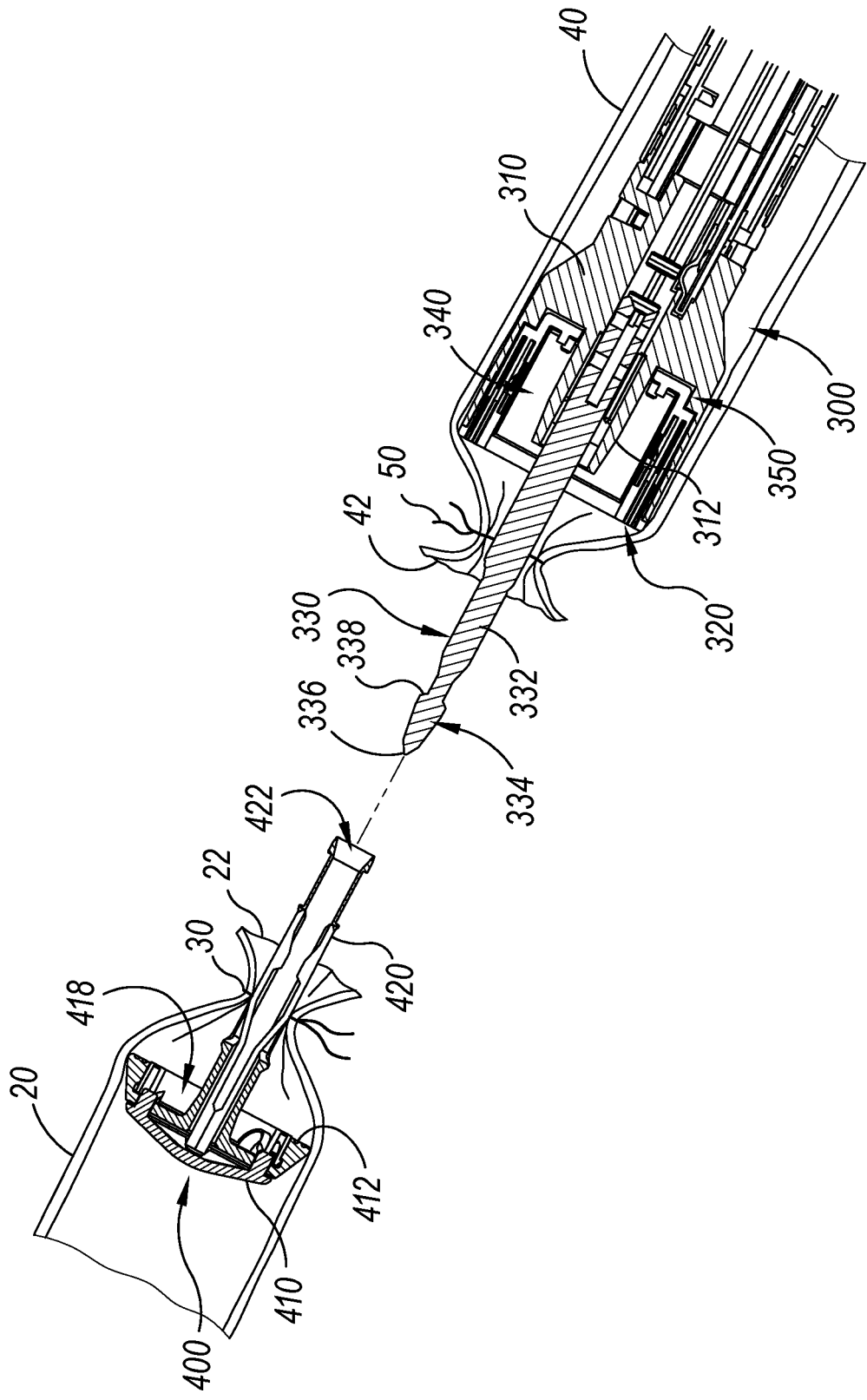
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
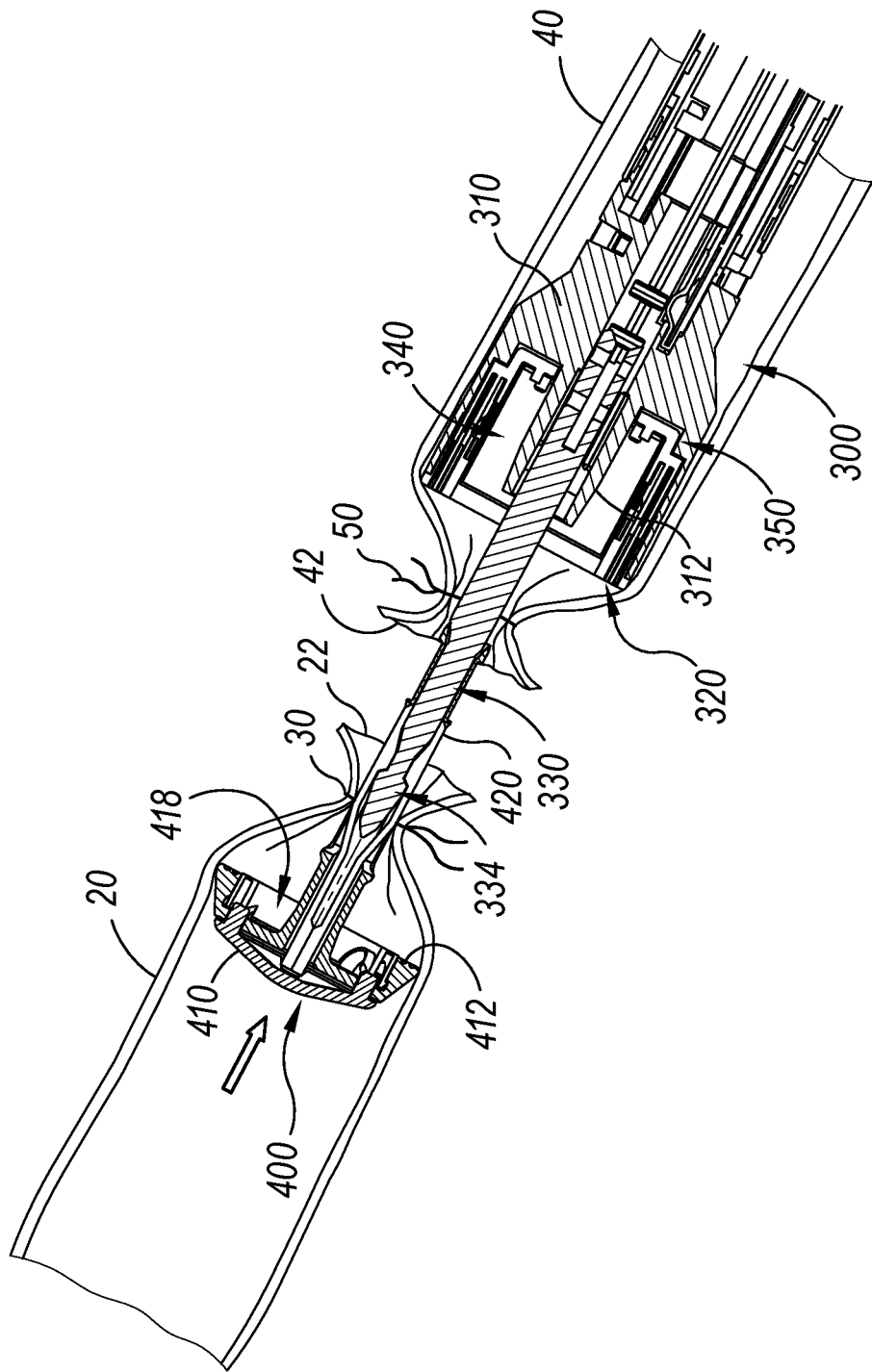
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
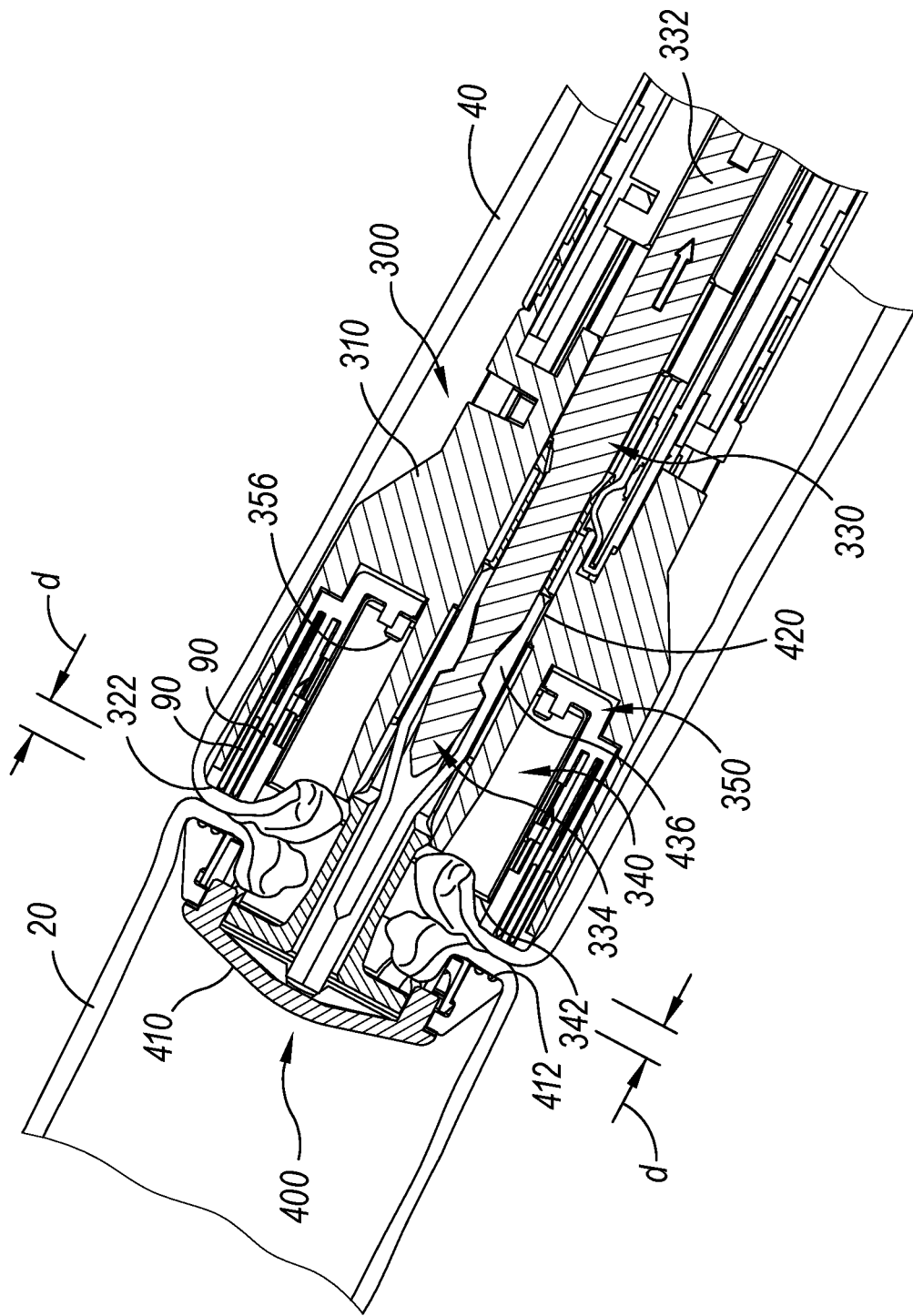
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
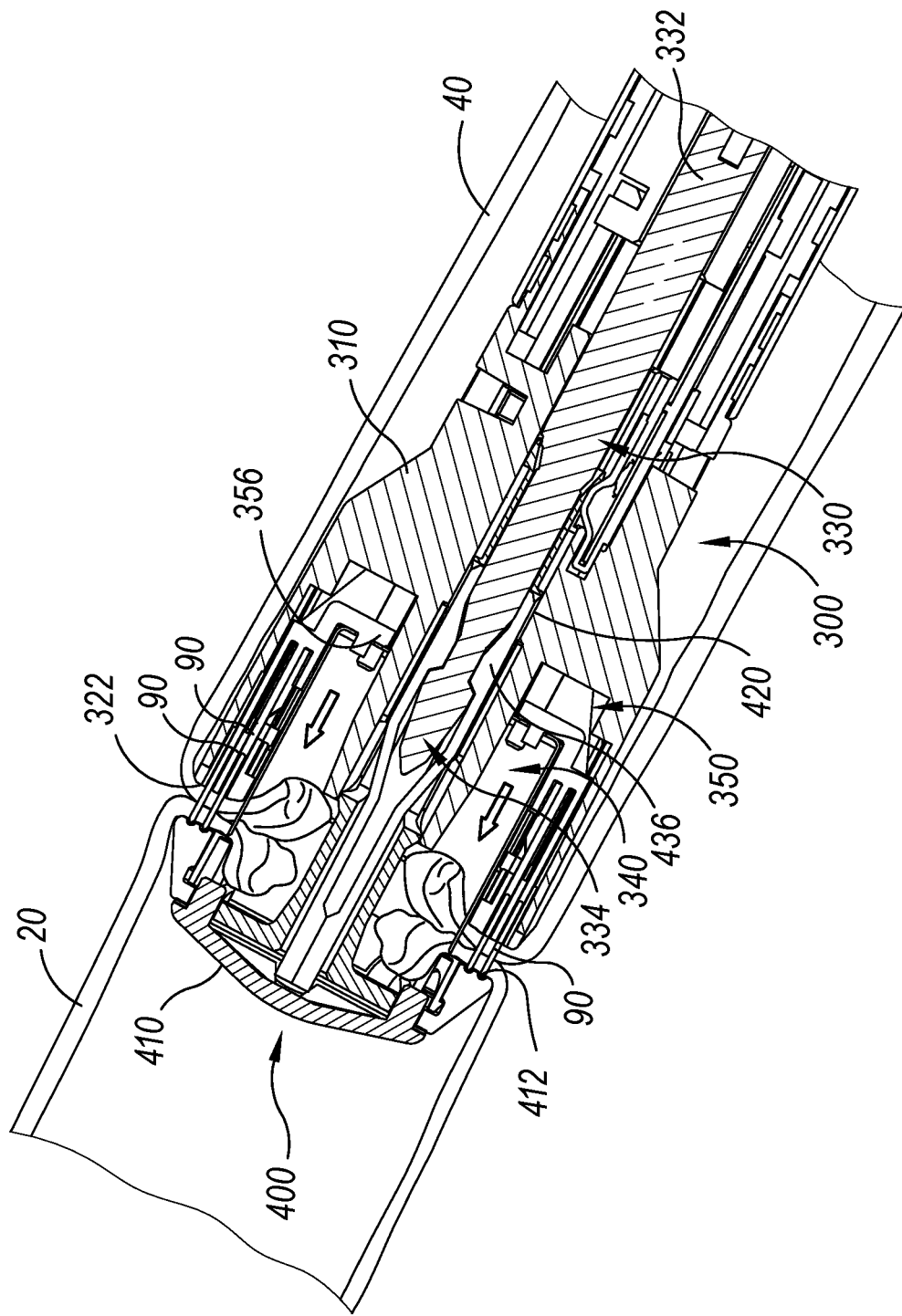
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
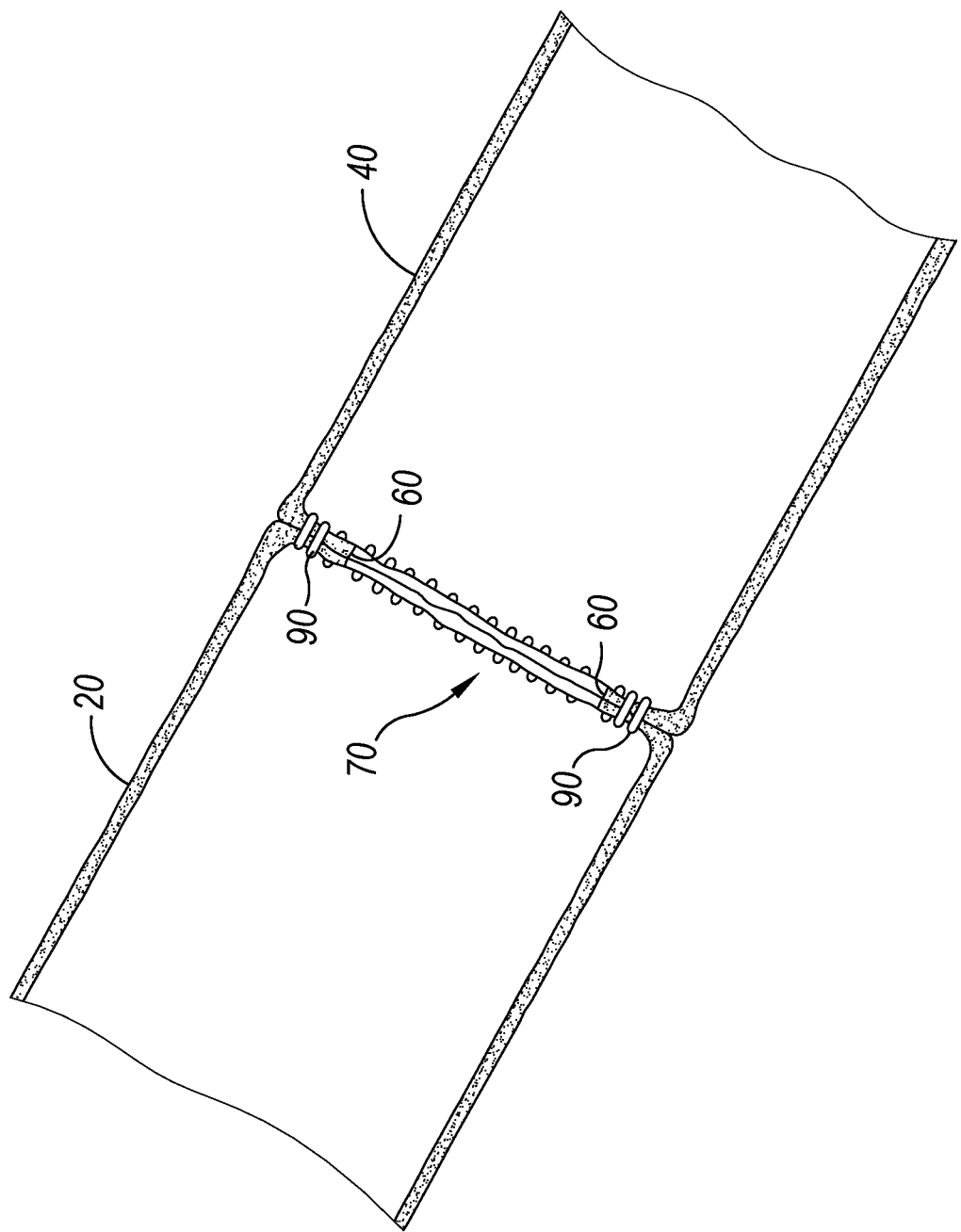
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary Alternative Features for Coupling Stapling Head Assembly with Shaft Assembly As noted above, tubular body member (310) of stapling head assembly (300) is fixedly secured to outer sheath (210) of shaft assembly (200) via sleeve (314). More specifically, sleeve (314) is permanently formed about a distal end portion of outer sheath (210) and a confronting proximal end portion of body member (310) via a process known as magneforming, which requires machinery that is complex and expensive to purchase and maintain.

In some manufacturing procedures, it may be desirable to provide an alternative secure connection between outer sheath (210) and body member (310) that does not require the complexity and expense of magneforming. An exemplary version of such a connection is shown in FIGS. 8-12C. As described in greater detail below, a body member assembly (510) includes a proximal housing (512) and a distal housing (514) that cooperate to provide a secure connection to a shaft assembly (600) that requires simplified manufacturing and assembly steps, such that the joining of body assembly (510) to shaft assembly (600) may be performed without complex and expensive machinery. Consequently, and advantageously, proximal housing (512) may be coupled with shaft assembly (600) at a first manufacturing facility without magneforming machinery, and subsequently distal housing (514) may be coupled with proximal housing (512) at the same facility or at a different second manufacturing facility without magneforming machinery. In some instances, the second step of coupling distal housing (514) with proximal housing (512) may even be performed by an end user on site. For instance, distal housing (514) may be pre-loaded with a cartridge that includes deck member (320), knife member (340), and staple driver member (350), where the resulting unit may be replaced by the end user after an initial use of circular stapling instrument (10).

Body member assembly (510) and shaft assembly (600) may be incorporated into circular surgical stapling instrument (10). It will be appreciated that components of body member assembly (510) and shaft assembly (600) are similar in structure and function to comparable components of circular stapling instrument (10) described above except as otherwise described. In particular, and as described in greater detail below, body member assembly (510) is configured to be removably coupled with a shaft assembly (600) with a simplified assembly process that does not require complex machinery.

Figure 8:
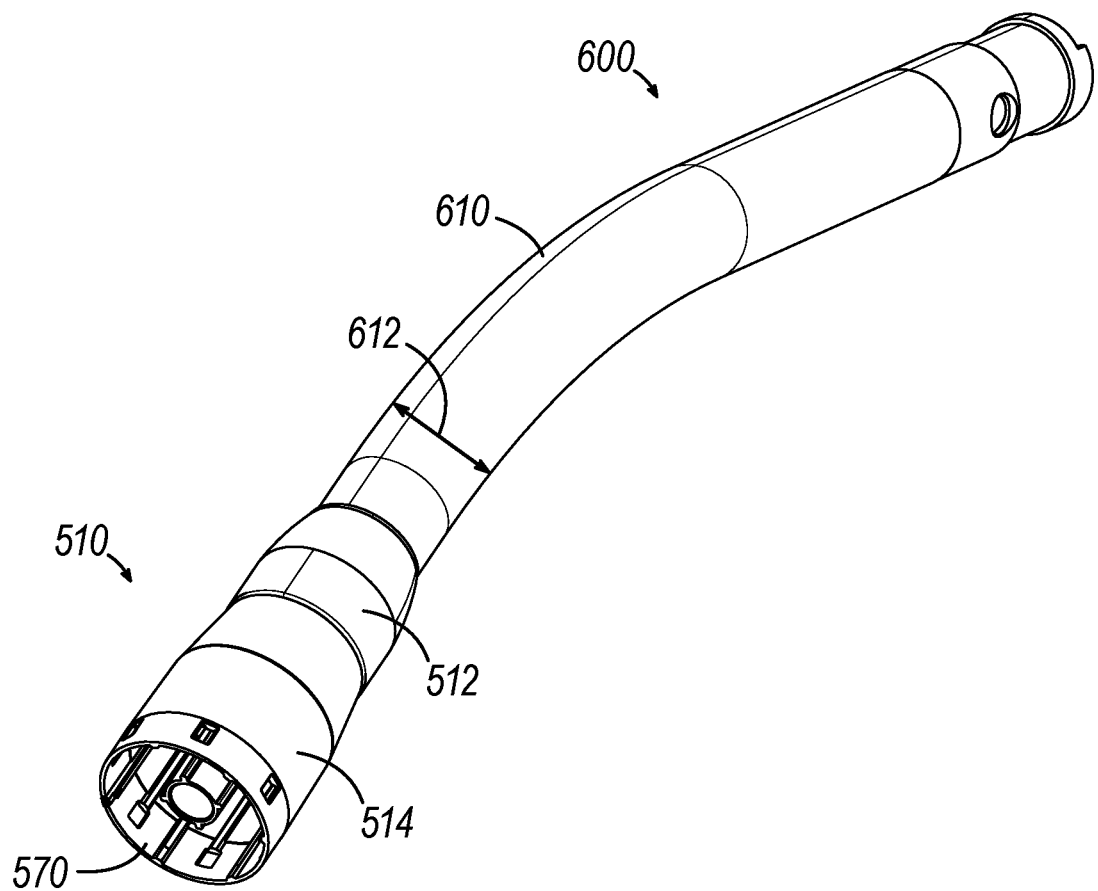
FIG. 8 depicts a perspective view of another exemplary body member assembly coupled to a shaft assembly for use with the circular stapler of FIG. 1.
Figure 9:
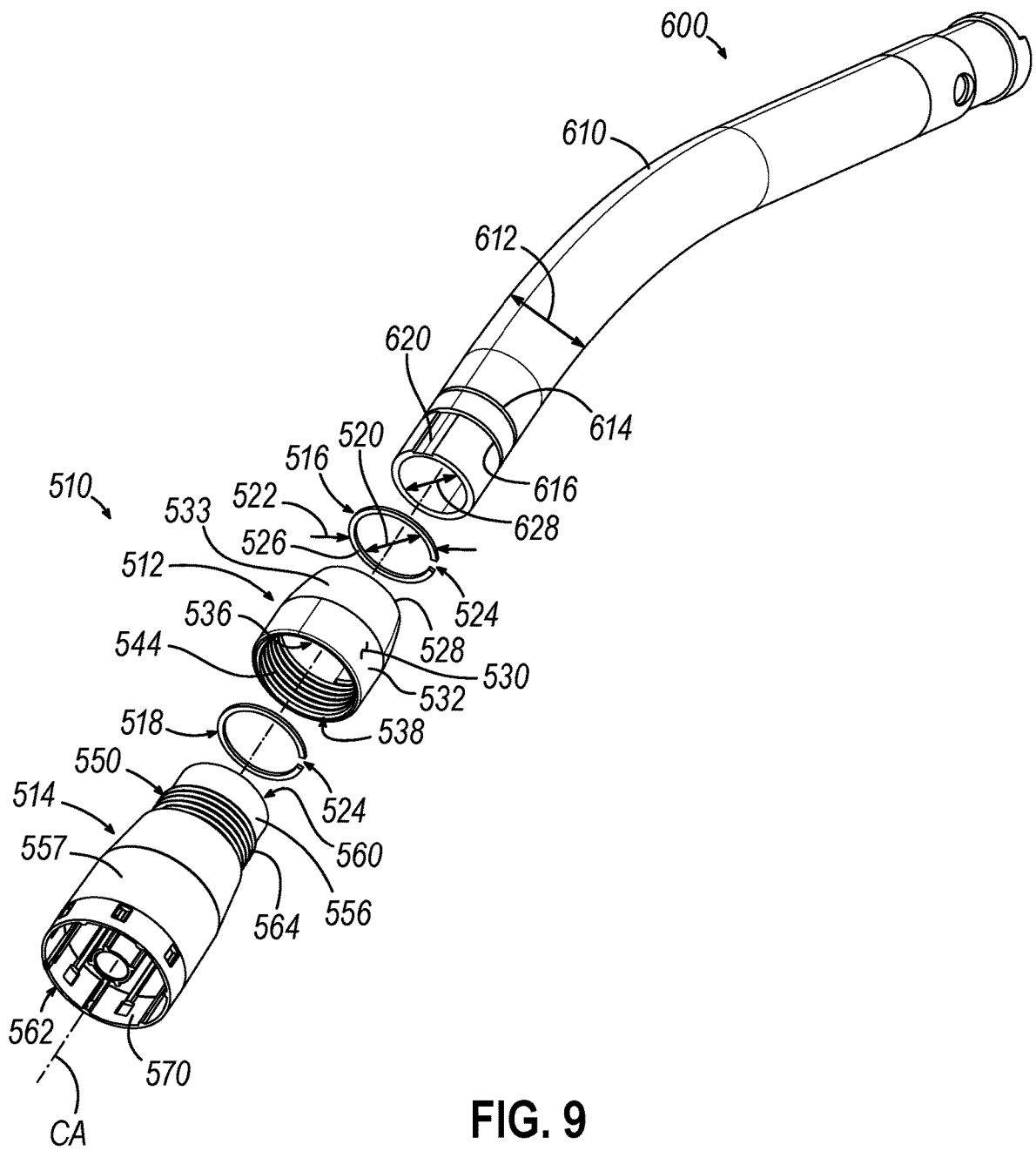
FIG. 9 depicts an exploded perspective view of the body member assembly and the shaft assembly of FIG. 8.

As shown in FIGS. 8 and 9, body member assembly (510) includes a proximal housing in the form of a collar (512), a distal housing in the form of a cartridge housing (514) having features similar to those of body member (310) described above, and a pair of retaining members (516, 518). Shaft assembly (600) includes an outer sheath (610) extending distally along a central axis (CA). Outer sheath (610) includes a pair of retaining grooves (614, 616) and a first mating feature in the form of a keyway (620). In other versions, the first mating feature may be in the form of a key, a spline, a facet, or any other structure known in the art to prevent the rotation of a first body relative to a second body. Keyway (620) may be formed by mechanically grinding, cutting, or milling away material from a distal portion of outer sheath (610), for example. Keyway (620) may also be formed with a mold or by additive manufacturing.

Retaining groves (614, 616) include a proximal retaining groove (614) and a distal retaining groove (616). Distal retaining groove (616) is positioned distally relative to proximal retaining groove (614) on outer sheath (610). Retaining grooves (614, 616) include an annular shape with a diameter that is smaller than an outer diameter (612) of outer sheath (610). Retaining groves (614, 616) may be produced by machining outer sheath (610) with a lathe and/or other suitable tool, for example. Pair of retaining groves (614, 616) may also be produced by casting outer sheath (610) within a mold or with additive manufacturing, which may require additional grinding, cutting or polishing. Proximal and distal retaining grooves (614, 616) are sized to accept proximal and distal retaining members, respectively, in the form of retaining rings (516, 518).

Each of retaining rings (516, 518) has an annular shape, an inner diameter (520), an outer diameter (522), and an open end (524). In other versions, the retaining members may include a crimp, a flare, a ferrule, or other structure known in the art to retain a collar on a tubular body. Retaining rings (516, 518) are resiliently biased towards an unexpanded position and are capable of being expanded from the unexpanded position to an expanded position. In the unexpanded position, inner diameter (520) is sized similarly to retaining groves (614, 616). In the expanded position, retaining rings (516, 518) are larger in diameter than outer diameter (612) of outer sheath (610). Retaining rings (516, 518) may be constructed of stainless steel, plastic, or any other surgically safe material known in the art to have resilient properties.

Proximal retaining ring (516) may be installed to outer sheath (610) by expanding proximal retaining ring (516) from the unexpanded position to the expanded position using snap ring pliers or another suitable tool. Inner diameter (520) of proximal retaining ring (516) is expanded to a larger diameter than outer diameter (612) of outer sheath (610). Once in the expanded position, proximal retaining ring (516) is slid proximally over outer sheath (610) until proximal retaining ring (516) aligns with proximal retaining groove (614). Proximal retaining ring (516) is released from the tool, thus allowing proximal retaining ring (516) to transition from the expanded position back to the unexpanded position within proximal retaining groove (614), thereby locking proximal retaining ring (516) within proximal retaining groove (614). Outer diameter (522) of proximal retaining ring (516) is larger than outer diameter (612) of outer sheath (610) and defines a distal face (526) that protrudes from outer diameter (612) of outer sheath (610). Distal face (526) is configured to engage a proximal end (528) of collar (512).

Collar (512) includes an external surface (530) having a first portion (532) extending proximally parallel to central axis (CA) and a second portion (533) that tapers inwardly in a proximal direction from first portion (532) to proximal end (528) of collar (512). In other versions, first and second portions (532, 533) may be sized differently. Collar (512) further includes a central bore having a proximal bore portion (536) and a distal bore portion (538) having a larger diameter than proximal bore portion (536). Proximal bore portion (536) extends distally from proximal end (528) of collar (512) along central axis (CA) to a transverse interior face (540), which defines an open distal end of proximal bore portion (536) and an open proximal end of distal bore portion (538). Distal bore portion (536) extends distally along central axis (CA) from transverse face (540) to distal end (534) of collar (512). includes a first fastening feature in the form of internal threads (544) having peaks and valleys arranged in a helical pattern. Collar (512) is slid proximally over the distal end of outer sheath (610) until proximal end (528) of collar (512) engages distal face (526) of proximal retaining ring (516), thus preventing collar (512) from translating proximally beyond proximal retaining ring (516), along central axis (CA), while still permitting collar (512) to rotate about central axis (CA).

Figure 10:
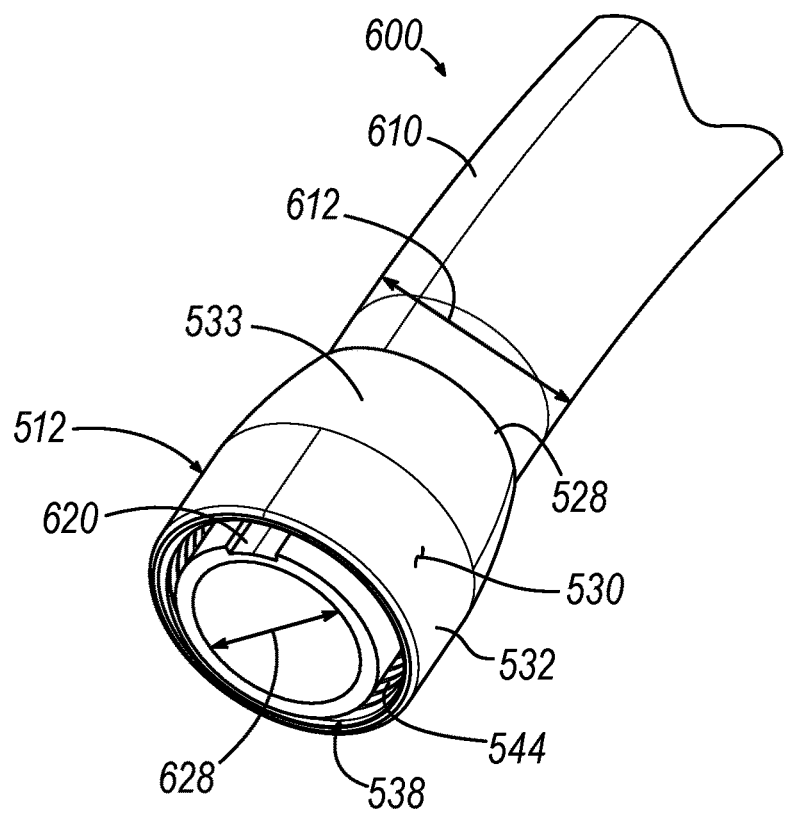
FIG. 10 depicts a perspective view of the shaft assembly of FIG. 8, viewed in a proximal direction.

As best shown in FIG. 10, distal retaining ring (518) is then installed proximally through distal bore portion (538), in the annular space around the distal end of outer sheath (610), and placed within distal retaining groove (616) in a manner similar to the installation of proximal retaining ring (516) described above. Distal retaining ring (518) defines a proximal face (548) which extends transversely from outer diameter (612) to outer sheath (610). Proximal face (548) engages transverse interior face (540) of collar (512) and prevents collar (512) from translating distally beyond distal retaining ring (518), along central axis (CA), while still permitting collar (512) to rotate about central axis (CA). Accordingly, as shown best in FIG. 12A, a proximal interior portion of collar (512) defined by proximal bore portion (536) is captured between proximal and distal retaining rings (516, 518), thereby constraining collar (512) longitudinally relative to outer sheath (610), along central axis (CA), while permitting collar (512) to freely rotate relative to outer sheath (610), about central axis (CA).

Figure 11:
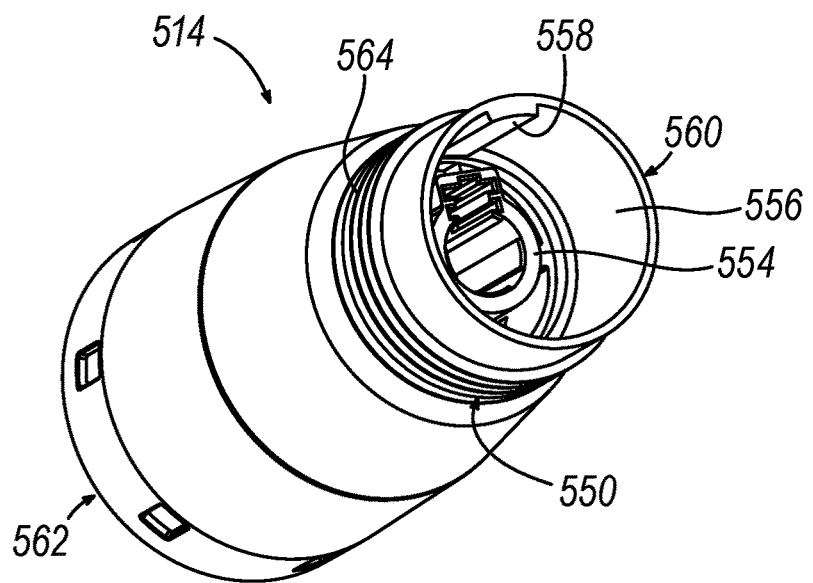
FIG. 11 depicts a perspective view of the body member assembly of FIG. 8, viewed in a distal direction.

As shown in FIGS. 9 and 11, cartridge housing (514) includes a second fastening feature in the form of external threads (564), a second mating feature in the form of a key (558), a proximal tube (556), and a core member (554)

extending along central axis (CA). Proximal tube (556) extends distally from a proximal end (560) of cartridge housing (514) to a distal portion (557) of cartridge housing (514) that supports core member (554) and defines a distal end (562) of cartridge housing (514). Distal portion (630) is sized larger than proximal tube (556). Key (558) extends radially inwardly from an inner surface of proximal tube (556) and longitudinally parallel to central axis (CA). Key (558) is configured to be mated with keyway (620) of outer sheath (610) to inhibit rotation of cartridge housing (514) relative to outer sheath (610) In other versions, the second mating feature may also include a spline, or a facet, that complements a spline or facet of the first mating feature of outer sheath (610).

External threads (564) of cartridge housing (514) extend radially outwardly from an outer surface of proximal tube (556) and longitudinally along central axis (CA) to distal end (562) of cartridge housing (514). External threads (564) have a plurality of peaks and valleys arranged helically and are configured to threadedly and releasably engage internal threads (544) of collar (512) as described below.

In other exemplary versions of body member assembly (510), the first and second fastening features may include various non-thread features suitable to facilitate a secure yet releasable connection between collar (512) and cartridge housing (514), where the first and second fastening features may incorporate features that engage in response to non-rotational movement. For instance, the first and second fastening features may include components that engage in response to linear movement, or a transverse movement to affix collar (512) to cartridge housing (514). In yet other versions, the first mating feature and the second mating feature may be reversed with key (558) positioned on outer sheath (610) and keyway (620) positioned on cartridge housing (514).

Figure 12A:
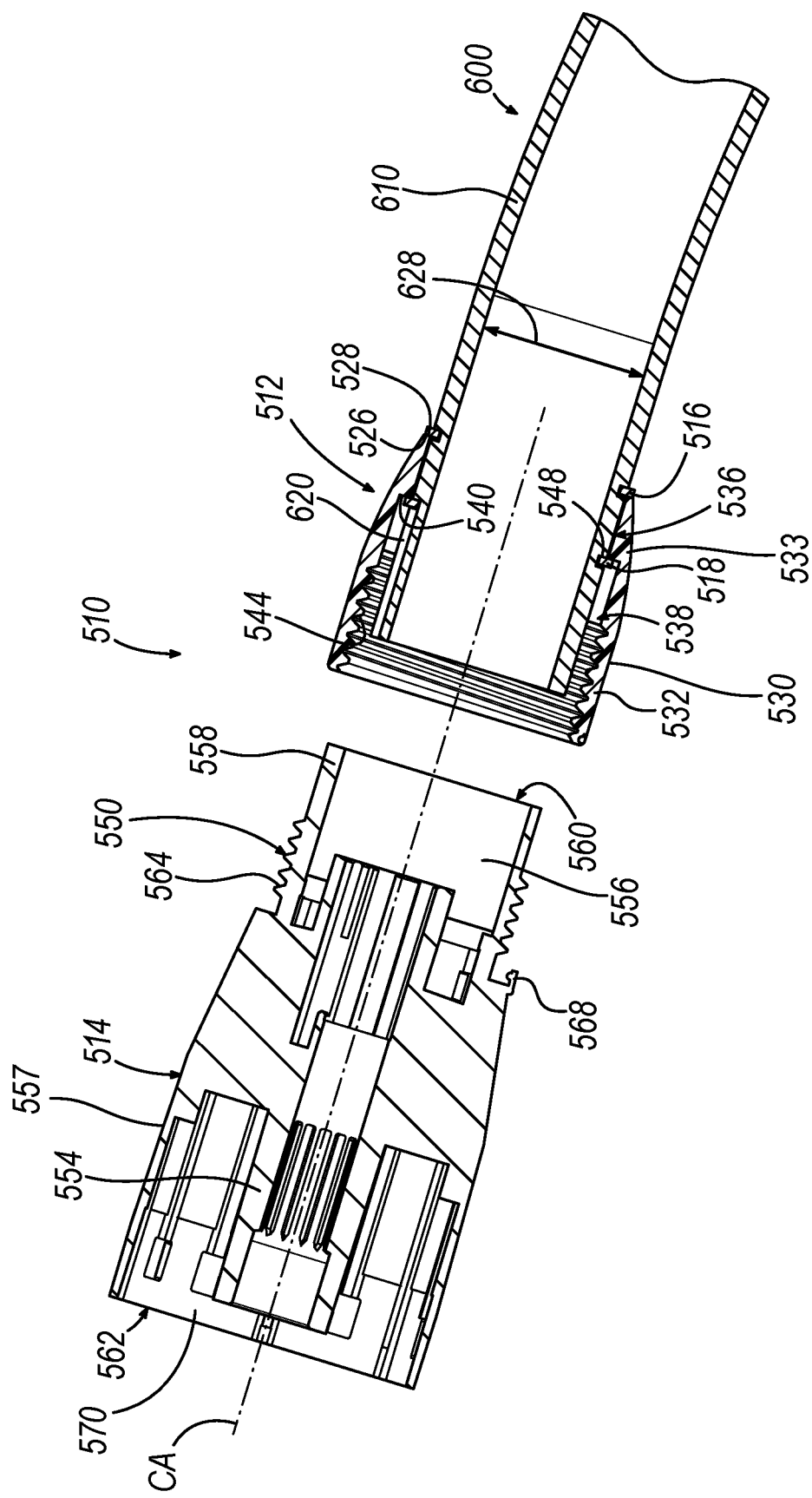
FIG. 12A depicts a cross-sectional side view of the body member assembly and the shaft assembly of FIG. 8, with a proximal housing coupled to the shaft assembly and a distal housing spaced apart from the proximal housing.

FIG. 12A shows cartridge housing (514) spaced apart from collar (512) and shaft assembly (600). Cartridge housing (514) is transitioned proximally while aligning proximal tube (556) of cartridge housing (514) with an inner diameter of collar (512). Proximal tube (556) is advanced proximally about a distal end of outer sheath (610) and within collar (512) such that keyway (620) of outer sheath (610) slidably receives key (558) of cartridge housing (514).

Figure 12B:
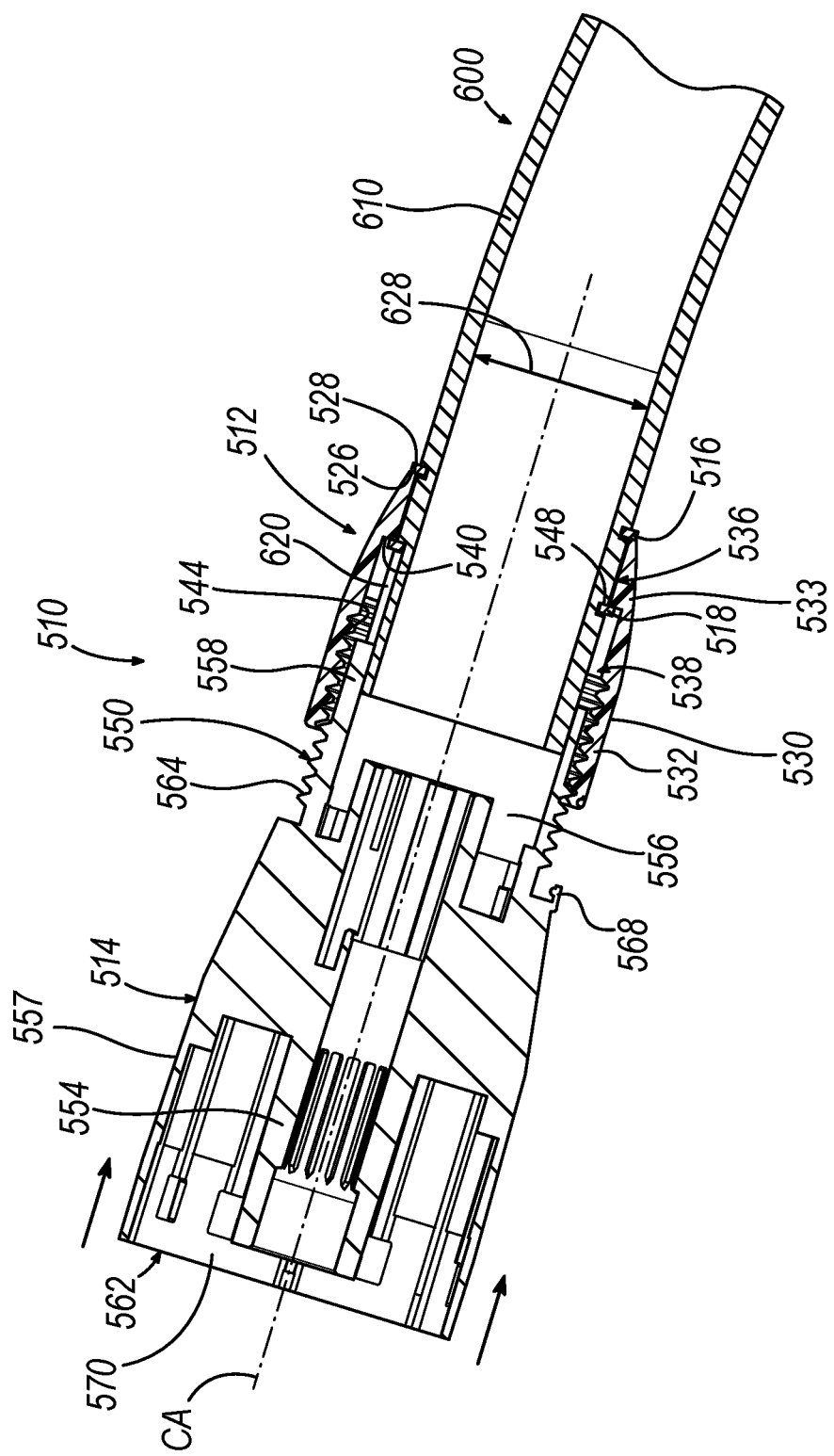
FIG. 12B depicts a cross-sectional side view of the body member assembly and the shaft assembly of FIG. 8, with the distal housing partially coupled to the proximal housing.

FIG. 12B shows proximal end (560) of cartridge housing (514) partially mated with collar (512) with proximal tube (556) positioned about outer sheath (610) such that key (558) is partially mated with keyway (620). Collar (512) is rotated about outer sheath (610) relative to cartridge housing (514) so that internal threads (544) engage external threads (564), thereby drawing cartridge housing (514) proximally towards outer sheath (610). In this manner, collar (512) functions as a rotatable coupling member to secure cartridge housing (514) to outer sheath (610). Meanwhile, key (558) and keyway (620) cooperate to inhibit relative rotation between cartridge housing (514) and outer sheath (610) while permitting cartridge housing (514) to advance proximally relative to outer sheath (610) toward a fully seated position.

Figure 12C:
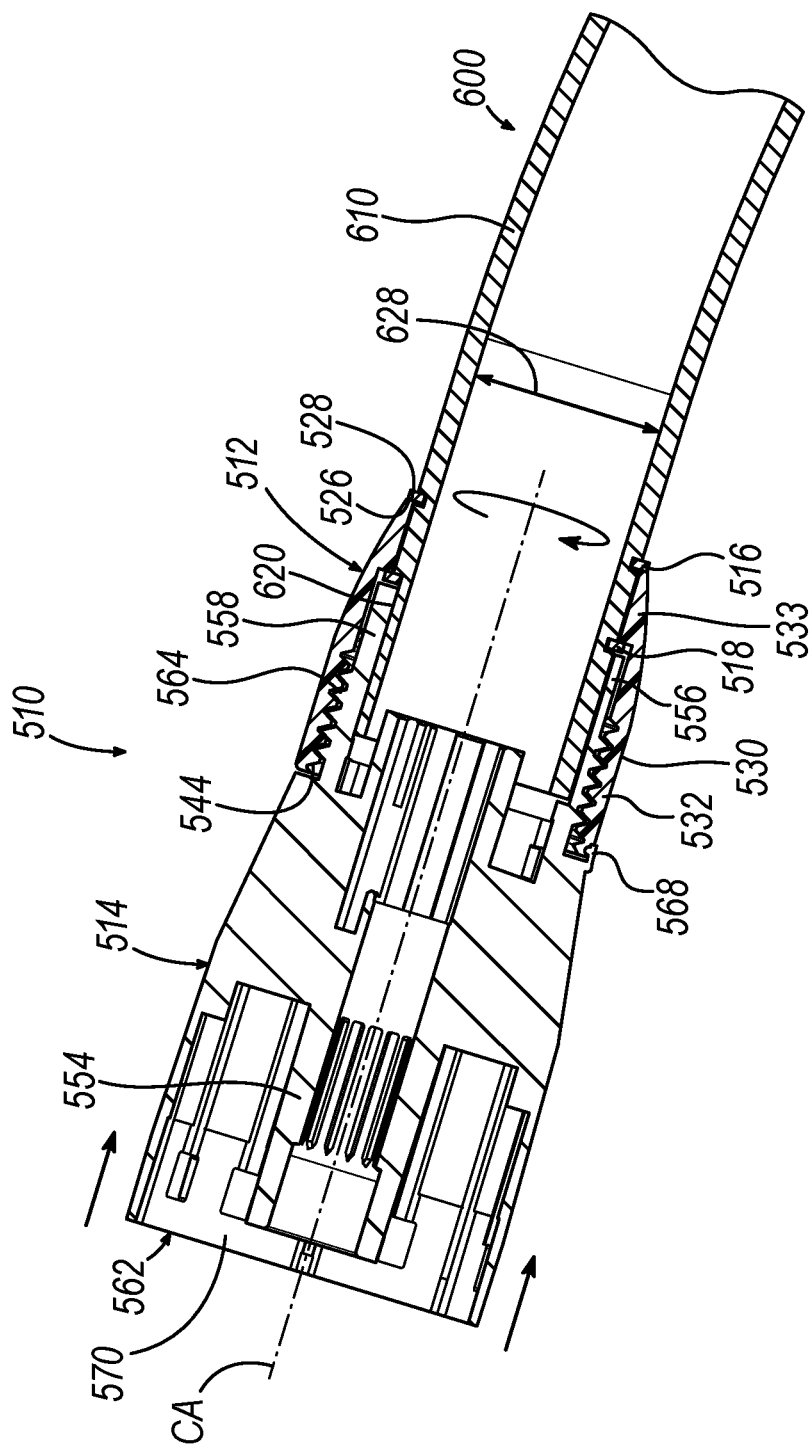
FIG. 12C depicts a cross-sectional side view of the body member and shaft assembly of FIG. 8, with the distal housing fully coupled to the proximal housing.

FIG. 12C shows cartridge housing (514) and collar (512) fully mated together and attached to outer sheath (610), which is achieved via further threaded engagement of collar (512) with cartridge housing (514), as described above. In this fully seated position of cartridge housing (514), distal end (562) of cartridge housing (514) confronts and engages proximal retaining ring (516) allowing internal threads (544) to tighten against external threads (564) fixedly attaching cartridge housing (514) to collar (512). In the present version, a proximal end of distal portion (557) of cartridge housing (514) includes a tab (568) configured to engage a corresponding feature on collar (512) to provide a "clicking" sound or a tactile sensation indicating that internal and external threads (544, 564) are fully tightened, and optionally to prevent further rotation of collar (512) in any direction.

Following attachment of cartridge housing (514) to outer sheath (610) in the manner described above, a cartridge that includes deck member (320) with staples (90), knife member (340), and staple driver member (350) may be installed proximally through an annular recess (570) of cartridge housing (514). Alternatively, cartridge housing (514) may be loaded with the cartridge through annular recess (570) while cartridge housing (514) is detached from collar (512) (shown in FIG. 12A), thus providing flexibility in the assembly process. In particular, cartridge housing (514) may be pre-loaded with the cartridge such that cartridge housing (514) and the cartridge as a unit are attached to shaft assembly (600) via the steps described above. In such versions, the engagement of key (558) of cartridge housing (514) with keyway (620) of outer sheath (610) may ensure that cartridge housing (514) and the cartridge are constrained in a predetermined rotational orientation relative to shaft assembly (600) that facilitates proper connection between components of the cartridge, such as staple driver member (350), and components of shaft assembly (600), such as stapling head assembly driver (240), as cartridge housing (514) is secured to outer sheath (610) via collar (512).

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument comprising: (a) a shaft assembly; (b) a stapling assembly disposed at a distal end of the shaft assembly and extending along a central axis, wherein the stapling assembly includes: (i) a housing assembly that includes a proximal housing and a distal housing, wherein the proximal housing is secured to the shaft assembly and is separable from the distal housing to thereby releasably couple the distal housing with the shaft assembly; (ii) a deck member having an annular array of staple openings configured to receive a plurality of staples, and (iii) a knife member at least partially disposed within the housing assembly; and (c) an anvil configured to selectively couple with the stapling assembly to compress a tissue and form staples in the tissue.

EXAMPLE 2

The surgical instrument of Example 1, wherein the distal housing includes a first mating feature, and the shaft assembly includes a second mating feature, wherein the first and second mating features are configured to engage each other to prevent the distal housing from rotating relative to the shaft assembly.

EXAMPLE 3

The surgical instrument of Example 2, wherein one of the first mating feature or the second mating feature includes a keyway the other of the first mating feature or the second mating feature includes a key configured to translate within the keyway.

EXAMPLE 4

The surgical instrument of any of the previous Examples, wherein the distal housing includes a bore having an inner diameter, wherein the shaft assembly includes an exterior diameter sized to fit within the inner diameter.

EXAMPLE 5

The surgical instrument of any of the previous Examples, wherein the proximal housing includes a collar, wherein the collar is configured to align coaxially with a distal end of the shaft assembly and rotate about the shaft assembly.

EXAMPLE 6

The surgical instrument of any of the previous Examples, wherein the shaft assembly includes at least one retaining groove.

EXAMPLE 7

The surgical instrument of Example 6, further comprising a retaining ring configured to seat within the at last one retaining groove to thereby constrain the collar longitudinally relative to the shaft assembly.

EXAMPLE 8

The surgical instrument of any of Example 7, wherein the retaining ring is configured to engage a proximal portion of the collar.

EXAMPLE 9

The surgical instrument of Example 7, wherein the at least one retaining groove comprises a proximal retaining groove and a distal retaining groove, wherein the retaining ring comprises a proximal retaining ring configured to seat within the proximal retaining groove to constrain the collar proximally relative to the shaft assembly, wherein the surgical instrument further includes a distal retaining ring configured to seat within the distal retaining groove to constrain the collar distally relative to the shaft assembly.

EXAMPLE 10

The surgical instrument of Example 9, wherein the distal retaining ring is configured to engage an interior feature of the collar.

EXAMPLE 11

The surgical instrument of any of the previous Examples, wherein the proximal housing includes a first fastening feature and the distal housing includes a second fastening feature, wherein the first and second fastening features are configured to engage one another to couple the distal housing with the proximal housing and the shaft assembly.

EXAMPLE 12

The surgical instrument of Example 11, wherein the first and second fastening features are configured to lockingly engage one another in response to relative rotation between the proximal housing and the distal housing.

EXAMPLE 13

The surgical instrument of any of Examples 11 through 12, wherein the first fastening feature is disposed on an interior of the proximal housing, wherein the second fastening feature is disposed on an exterior of the distal housing.

EXAMPLE 14

The surgical instrument of any of Examples 11 through 13, wherein the first fastening feature includes internal threads, and the second fastening feature includes external threads.

EXAMPLE 15

The surgical instrument of any of Examples 11 through 14, wherein the distal housing includes a first mating feature and the shaft assembly includes a second mating feature configured to engage one another to inhibit relative rotation between the distal housing and the shaft assembly, wherein the first mating feature is configured to engage the second mating feature to align the distal housing with the shaft assembly before the first fastening feature engages the second fastening feature.

EXAMPLE 16

A surgical instrument comprising: (a) a shaft assembly; (b) a stapling assembly disposed at a distal end of the shaft assembly and defining a central axis, wherein the stapling assembly includes an annular array of openings that house a plurality of staples; (c) an anvil configured to releasably couple with the stapling assembly to compress, staple, and cut tissue positioned between the anvil and the stapling assembly; and (d) a rotatable coupling member secured to the distal end of the shaft assembly, wherein the rotatable coupling member is rotatable relative to the shaft assembly and about the central axis to couple the distal end of the shaft assembly with a proximal end of the stapling assembly.

EXAMPLE 17

The surgical instrument of Example 16, further including a pair of retaining rings, wherein the retaining rings are fixedly coupled to the shaft assembly and are configured to prevent the rotatable coupling member from axially translating relative to the shaft assembly.

EXAMPLE 18

The surgical instrument of any of Examples 16 through 17, wherein the rotatable coupling member includes a first helical feature, and the proximal end of the stapling assembly includes a second helical feature, wherein the first helical feature is configured to engage the second helical feature in response to rotation of the rotatable coupling member to thereby couple the stapling assembly with the shaft assembly.

EXAMPLE 19

The surgical instrument of any of Examples 16 through 18, wherein the shaft assembly includes a first alignment feature and the stapling assembly includes a second alignment feature, wherein one of the first or second alignment features is configured to translate within the other of the first and second alignment features in response to rotation of the rotatable coupling member relative to the stapling assembly.

EXAMPLE 20

A surgical instrument comprising: (a) a shaft assembly; and (b) a stapling assembly disposed at a distal end of the shaft assembly and extending distally along a central axis, wherein the stapling assembly includes: (i) a deck surface including an annular array of staple openings configured to receive a plurality of staples, (ii) a knife member configured to cut tissue, (iii) a distal housing configured to support the deck surface and slidably receive the knife member, and (iv) a proximal housing configured to threadedly engage the distal housing and thereby couple the distal housing with the shaft assembly.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:
1. A surgical instrument comprising:
(a) a shaft assembly including at least two retaining grooves;
(b) at least two retaining members positioned within the at least two retaining grooves;
(c) a stapling assembly disposed at a distal end of the shaft assembly and extending along a central axis, wherein the stapling assembly includes:
(i) a housing assembly that includes a proximal housing and a distal housing, wherein the proximal housing is longitudinally constrained relative to the shaft assembly by the at least two retaining members and is separable from the distal housing to thereby releasably couple the distal housing with the shaft assembly;

(ii) a deck member having an annular array of staple openings configured to receive a plurality of staples, and (iii) a knife member at least partially disposed within the housing assembly; and (d) an anvil configured to selectively couple with the stapling assembly to compress a tissue and form staples in the tissue.

2. The surgical instrument of claim 1, wherein the distal housing includes a first mating feature, and the shaft assembly includes a second mating feature, wherein the first and second mating features are configured to engage each other to inhibit the distal housing from rotating relative to the shaft assembly.

3. The surgical instrument of claim 2, wherein one of the first mating feature or the second mating feature includes a keyway the other of the first mating feature or the second mating feature includes a key configured to translate within the keyway.

4. The surgical instrument of claim 1, wherein the distal housing includes a bore having an inner diameter, wherein the shaft assembly includes an exterior diameter sized to fit within the inner diameter.

5. The surgical instrument of claim 1, wherein the proximal housing includes a collar, wherein the collar is configured to align coaxially with a distal end of the shaft assembly and rotate about the shaft assembly.

6. The surgical instrument of claim 5, wherein the at least two retaining groves include an annular shape recessed within the shaft assembly.

7. The surgical instrument of claim 6, wherein the at least two retaining members comprise a retaining ring configured to seat within the at least one retaining groove to thereby constrain the collar longitudinally relative to the shaft assembly, wherein the retaining ring is separate and apart from the collar.

8. The surgical instrument of claim 7, wherein each retaining ring is configured to engage a proximal portion of the collar.

9. The surgical instrument of claim 7, wherein the at least two retaining groves include a proximal retaining groove and a distal retaining groove, wherein each retaining ring comprises a proximal retaining ring configured to seat within the proximal retaining groove to constrain the collar proximally relative to the shaft assembly, wherein the surgical instrument further includes a distal retaining ring configured to seat within the distal retaining groove to constrain the collar distally relative to the shaft assembly.

10. The surgical instrument of claim 9, wherein the distal retaining ring is configured to engage an interior feature of the collar.

11. The surgical instrument of claim 1, wherein the proximal housing includes a first fastening feature and the distal housing includes a second fastening feature, wherein the first and second fastening features are configured to engage one another to couple the distal housing with the proximal housing and the shaft assembly.

12. The surgical instrument of claim 11, wherein the first and second fastening features are configured to lockingly engage one another in response to relative rotation between the proximal housing and the distal housing.

13. The surgical instrument of claim 11, wherein the first fastening feature is disposed on an interior of the proximal housing, wherein the second fastening feature is disposed on an exterior of the distal housing.

14. The surgical instrument of claim 13, wherein the first fastening feature includes internal threads, and the second fastening feature includes external threads.

15. The surgical instrument of claim 11, wherein the distal housing includes a first mating feature and the shaft assembly includes a second mating feature configured to engage one another to inhibit relative rotation between the distal housing and the shaft assembly, wherein the first mating feature is configured to engage the second mating feature to align the distal housing with the shaft assembly before the first fastening feature engages the second fastening feature.

16. A surgical instrument comprising:

(a) a shaft assembly;

(b) a stapling assembly disposed at a distal end of the shaft assembly and defining a central axis, wherein the stapling assembly includes an annular array of openings that house a plurality of staples;

(c) an anvil configured to releasably couple with the stapling assembly to compress, staple, and cut tissue positioned between the anvil and the stapling assembly;

(d) a rotatable coupling member secured to the distal end of the shaft assembly, wherein the rotatable coupling member is rotatable relative to the shaft assembly and about the central axis to couple the distal end of the shaft assembly with a proximal end of the stapling assembly; and (e) a pair of retaining rings coupled to the shaft assembly, wherein the retaining rings are configured to inhibit the rotatable coupling member from longitudinally translating relative to the shaft assembly.

17. The surgical instrument of claim 16, wherein the rotatable coupling member includes a first helical feature, and the proximal end of the stapling assembly includes a second helical feature, wherein the first helical feature is configured to engage the second helical feature in response to rotation of the rotatable coupling member to thereby couple the stapling assembly with the shaft assembly.

18. The surgical instrument of claim 16, wherein the shaft assembly includes a first alignment feature and the stapling assembly includes a second alignment feature, wherein one of the first or second alignment features is configured to translate within the other of the first and second alignment features in response to rotation of the rotatable coupling member relative to the stapling assembly.

19. A surgical instrument comprising:

(a) a shaft assembly including a distal retaining member and a proximal retaining member; and (b) a stapling assembly disposed at a distal end of the shaft assembly and extending distally along a central axis, wherein the stapling assembly includes:

(i) a deck surface including an annular array of staple openings configured to receive a plurality of staples, (ii) a knife member configured to cut tissue, (iii) a distal housing configured to support the deck surface and slidably receive the knife member, and (iv) a proximal housing configured to threadedly engage the distal housing and thereby couple the distal housing with the shaft assembly, wherein the distal retaining member is configured to engage the proximal housing to inhibit the proximal housing from distally translating relative to the shaft assembly, and the proximal retaining member is configured to engage the proximal housing to inhibit the proximal housing from proximally translating relative to the shaft assembly.

20. The surgical instrument of claim 19, wherein the shaft assembly includes a proximal retaining groove and a distal retaining groove, wherein the distal retaining member is seated and longitudinally constrained within the distal retaining groove and the proximal retaining member is seated and longitudinally constrained within the proximal retaining groove.

* * * * *